United States Patent
Pingel et al.

(10) Patent No.: US 11,844,350 B2
(45) Date of Patent: Dec. 19, 2023

(54) PLANT GROWTH REGULATION

(71) Applicant: Syngenta Participations AG, Basel (CH)

(72) Inventors: Arne Pingel, Basel (CH); Nicolas Schmitt, Basel (CH); Anbu Bharathi Thayumanavan, Hyderabad (IN)

(73) Assignee: SYNGENTA PARTICIPATIONS AG, Basel (CH)

( * ) Notice: Subject to any disclaimer, the term of this patent is extended or adjusted under 35 U.S.C. 154(b) by 418 days.

(21) Appl. No.: 16/772,537

(22) PCT Filed: Nov. 21, 2018

(86) PCT No.: PCT/EP2018/082133
§ 371 (c)(1),
(2) Date: Jun. 12, 2020

(87) PCT Pub. No.: WO2019/115193
PCT Pub. Date: Jun. 20, 2019

(65) Prior Publication Data
US 2020/0383332 A1   Dec. 10, 2020

(30) Foreign Application Priority Data
Dec. 12, 2017   (IN) .............................. 201711044599

(51) Int. Cl.
*A01N 43/90* (2006.01)
*A01N 37/08* (2006.01)
*A01N 37/42* (2006.01)
*C07D 473/40* (2006.01)

(52) U.S. Cl.
CPC ............. *A01N 43/90* (2013.01); *A01N 37/08* (2013.01); *A01N 37/42* (2013.01); *C07D 473/40* (2013.01)

(58) Field of Classification Search
None
See application file for complete search history.

(56) References Cited

U.S. PATENT DOCUMENTS

| | | | |
|---|---|---|---|
| 8,222,260 B2 | 7/2012 | Spichal et al. | |
| 10,517,301 B2 | 12/2019 | Rees et al. | |
| 2014/0213453 A1* | 7/2014 | Haas | A01N 43/653 504/144 |

FOREIGN PATENT DOCUMENTS

| | | |
|---|---|---|
| CN | 108432777 A | 8/2018 |
| EP | 0155911 A1 | 9/1985 |
| JP | S615080 A | 1/1986 |
| JP | 2008127316 A | 6/2008 |
| JP | 2010531818 A | 9/2010 |
| JP | 2014530178 A | 11/2014 |
| JP | 2014532707 A | 12/2014 |
| WO | 2009003428 A2 | 1/2009 |
| WO | 2012031574 A1 | 3/2012 |
| WO | 2016095881 A1 | 6/2016 |
| WO | 2017215981 A1 | 12/2017 |
| WO | 2017216003 A1 | 12/2017 |
| WO | 2017216005 A1 | 12/2017 |

OTHER PUBLICATIONS

International Search Report for International Patent Application No. PCT/EP2018/082133, dated Jan. 2, 2019.
Bertolin et al., Aumento da Produtividade de Soja com a Aplicacao de Bioestimulantes, Bragantia, Campinas, Jun. 30, 2010, pp. 339-347, vol. 69, n.2.
Zatloukal et al.—Novel potent inhibitors of *A. thaliana* cytokinin oxidase/dehydrogenase—Bioorganic and Medicinal Chemistry 16 (2008)—pp. 9268-9275.
MODDUS 250 EC. Syngenta Label.
English Abstract corresponding to CN108432777, (Year: 2018).
Aremu et al.; "Physiological responses and endogenous cytokinin profiles of tissue-cultured Williams bananas in relation to roscovitine and an inhibitor of cytokinin oxidase/dehydrogenase (INCYDE) treatments"; Planta 2012; 236; 6; pp. 1775-1790, (Year: 2012).

* cited by examiner

*Primary Examiner* — Bethany P Barham
*Assistant Examiner* — Barbara S Frazier
(74) *Attorney, Agent, or Firm* — BakerHostetler; Toni-Junell Herbert

(57) ABSTRACT

The present invention relates to a new plant growth regulation composition comprising a compound of Formula (Ia) and trinexapac-ethyl. (Ia). It also relates to a method for enhancing or regulating the growth of plants comprising applying said composition.

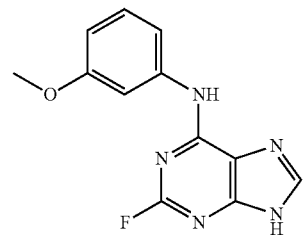

(Ia)

8 Claims, No Drawings

PLANT GROWTH REGULATION

CROSS-REFERENCE TO RELATED APPLICATIONS

This application is a 371 National Stage application of International Application No. PCT/EP2018/082133, filed Nov. 21, 2018, which claims priority to IN 201711044599 filed Dec. 12, 2017, the entire contents of which applications are hereby incorporated by reference.

The present invention relates to a new plant growth regulation composition. It also relates to a method for enhancing or regulating the growth of plants comprising applying said composition.

Plant growth regulators are often used to regulate the growth and development of crop plants. For example, plant growth regulators are used to slow the development of a crop (such as oil seed rape) so that it flowers at a desired time, reduce the height of a crop (such as in cereals) so that it is less susceptible to lodging, increase nitrogen efficiency, regulate flowering and fruit set of a crop (such as fruit trees), and slow turfgrass growth rate to reduce mowing frequency.

There are several different classes of plant growth regulator. Known classes include azoles (such as uniconazole, and paclobutrazol), cyclohexane carboxylates (such as trinexapac-ethyl, and prohexadione-calcium), pyrimidinyl carbinols (such as flurprimidol, and ancymidol), quarternary ammoniums (such as chlormequat-chloride, and mepiquat-chloride), and sulphonyl-amino phenyl-acetamides (such as mefluidide).

Plant growth regulators operate by various modes of action. For example, onium-type plant growth retardants such as chlormequat-chloride and mepiquat-chloride, that possess a positively charged ammonium, phosphonium or sulphonium group, function by blocking the synthesis of gibberellin early in the biosynthetic pathway. Growth retardants comprising a nitrogen-containing heterocycle, such as flurprimidol, paclobutrazol and uniconazole-P, act as inhibitors of monooxygenases that catalyse oxidative steps in gibberellin biosynthesis. Structural mimics of 2-oxoglutaric acid, such as the acylcyclohexanediones trinexapac-ethyl and prohexadione-calcium, interfere with the late steps of gibberellin biosynthesis. Other plant growth regulators, such as mefluidide, inhibit cell division and differentiation.

Plant growth regulators such as trinexapac-ethyl are commonly used on crops to reduce the risk of lodging through stem thickening and shortening, and improved rooting. Lodging can adversely affect plant growth and development, for example reducing photosynthetic capabilities and ultimately yield. Lodging can also lead to difficulties for harvesting, because a flattened crop is difficult to harvest and leads to poor grain quality and yield loss. Lodging also contributes to uneven maturity of the crop, and high moisture content, which leads to further harvest problems.

There is a need for new plant solutions for regulating the growth of plants, and reducing or controlling lodging.

According to the present invention, there is provided a method for regulating the growth of crop plants, wherein the method comprises applying to the plants, plant part, plant propagation material or plant growing locus a compound of Formula (I),

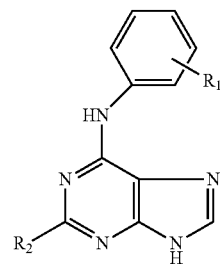

(I)

wherein $R_1$ denotes one to five substituents independently selected from the group consisting of hydrogen, halogen, hydroxyl, amino, alkyloxy and alkyl;
and $R_2$ is selected from the group consisting of amino, halogen, nitro, thio, alkylthio and alkyl;
or a composition comprising said compound.

In a further embodiment of the present invention, there is provided a method for reducing lodging of a crop, comprising applying to the plants, plant part, plant propagation material or plant growing locus, a compound of Formula (I),

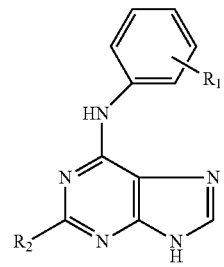

(I)

wherein $R_1$ denotes one to five substituents independently selected from the group consisting of hydrogen, halogen, hydroxyl, amino, alkyloxy and alkyl;
and $R_2$ is selected from the group consisting of amino, halogen, nitro, thio, alkylthio and alkyl;
or a composition comprising said compound.

In certain compounds of Formula (I), $R_1$ is methoxy. In certain compounds of formula (I), $R_2$ is halogen. In certain compounds of Formula (I), $R_1$ is methoxy and $R_2$ is halogen. In certain compounds of Formula (I), $R_2$ is fluorine.

In one embodiment, the compound is Formula (Ia):

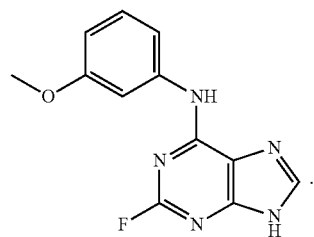

(Ia)

In one embodiment, the compound of Formula I is applied during the reproductive growth stage of the crop plants.

Regulation of plant growth and/or lodging may be particularly effective when the plant is subject to abiotic stress conditions. In one embodiment, the crop plants are subject to abiotic stress such as heat, cold or drought stress at the time of application.

In one embodiment, the compound of Formula (I) is applied in an amount that is sufficient to regulate the growth of the plant and/or to reduce lodging.

In a further aspect of the invention, there is provided the use of a compound of Formula (I) according to the invention as a plant growth regulator and/or for reduction of lodging.

According to the present invention, "regulating the growth of a plant" means controlling growth to improve crop yield, for example by improving, for example plant physiology, plant growth and development and/or plant architecture. In particular, it refers to reducing plant height, and/or improving rooting, which are beneficial features in crops or conditions where there is a risk of lodging.

In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

The present invention may also lead to an improvement in harvestability of the crop, for example due to better plant stand and reduced lodging, which in turn may result in improved yield and/or grain quality.

The term "reducing lodging" refers to reducing the displacement of stems or roots from their vertical and proper placement.

The term "plant propagation material" denotes all the generative parts of the plant, such as seeds, which can be used for the multiplication of the latter and vegetative plant materials such as cuttings and tubers. In particular, there may be mentioned the seeds, roots, fruits, tubers, bulbs, and rhizomes.

The term "plants" refers to all physical parts of a plant, including seeds, seedlings, saplings, roots, tubers, stems, stalks, foliage, and fruits.

The term "locus" as used herein means fields in or on which plants are growing, or where seeds of cultivated plants are sown, or where seed will be placed into the soil. It includes soil, seeds, and seedlings, as well as established vegetation.

The term "reproductive growth stage" refers to the final stage of plant growth which follows germination and vegetative growth. During the reproductive growth stage, the plant's energy is directed to the production of flowers, fruits and seeds. The reproductive growth stage typically starts at the beginning of stem elongation (BBCH 30). In rice, it includes panicle initiation (BBCH 30), panicle formation (BBCH 32), internode elongation (BBCH 34), spikelet differentiation (BBCH 35), meiosis (BBCH 39), booting (BBCH 41-49), and heading (BBCH 51). In wheat, the reproductive growth stage includes first node formation (BBCH 31), flag leaf formation (BBCH 37), booting (BBCH 41-49), and heading (BBCH 50-59).

In one embodiment, the crop plants are at a BBCH growth stage from 30 to 51 at the time of treatment. In a further embodiment, the crop plants are at a BBCH growth stage from 30 to 40 at the time of treatment. In one embodiment, the crop plants are treated after the start of the reproductive growth stage. In a further embodiment, the crop plants are treated before the heading growth stage, corresponding to BBCH growth stage 51.

Where a range of numbers is disclosed herein (for example, 1 to 10), this is intended to include all numbers and intervening values within that range (for example, 1, 1.1, 2, 3, 3.9, 4, 5, 6, 6.5, 7, 8, 9 and 10) and also any sub-range of numbers and intervening values within that range (for example, 2 to 8, 1.5 to 5.5 and 3.1 to 4.7). Additionally, it is intended that the both the upper and lower limits specified are included within the range.

Where ranges or values used herein are preceded by the term "about", this term is intended to provide support for both the exact number that it precedes, and also a number that is near to or approximately the number that it precedes. In determining whether a number is near to or approximately a specifically recited number, the near or approximating number may be a number, which would be rounded to or be substantially equivalent to the specifically recited number. For example, the term "about 5" includes 5.0, 4.5, 5.4, 4.92, 5.01, and so on.

The rates of application of the compound of Formula (I) may vary within wide limits and depend on the nature of the soil, the method of application (pre- or post-emergence; seed dressing; application to the seed furrow; no tillage application, etc.), the crop plant, the prevailing climatic conditions, and other factors governed by the method of application, the time of application and the target crop. For foliar or drench application, the compound of Formula (I) is generally applied at a rate of from 1 to 2000 g active ingredient/ha, especially from 1 to 1000 g AI/ha, 1 to 500 g AI/ha, 1 to 100 g AI/ha. In one embodiment, the compound of Formula (I) is applied at a rate from 5 to 50 g AI/ha, form 5 to 30 g AI/ha, from 10 to 30 g AI/h, or from 10 to 20 g AI/ha. In one embodiment, the compound of Formula (I) is applied at about 10 g AI/ha. In a further embodiment, the compound of Formula (I) is applied at about 20 g AI/ha.

In one embodiment of the invention, there is provided a method of treating a plant propagation material comprising applying to the plant propagation material a compound of Formula (I) as defined in claim 1, or a composition comprising a compound of Formula (I) in an amount effective to regulate plant growth and/or reduce plant lodging. For treatment of seeds, the rate of application is generally between 0.0005 and 150 g AI per 100 kg of seed.

In one embodiment, the plant growth regulating or lodging reducing composition according to the invention is a composition that is a seed treatment composition or a seed coating composition. The compositions according to the invention may also further comprise one or more insecticidal, acaracidal, nematicidal or fungicidal active ingredients.

In a further embodiment, the compound of Formula (I) according to the invention is for use in a foliar or a seed treatment composition.

Preferably, the plant propagation material of the invention is a seed. In one embodiment the seed is a corn (maize) seed.

In a further embodiment of the present invention, there is provided a method for regulating the growth of plants and/or reducing lodging of a crop, comprising applying to the plants, plant part, plant propagation material or plant growing locus during the reproductive growth stage of the crop, a composition comprising a compound of Formula (I) and trinexapac-ethyl. In particular the composition may comprise the compound of Formula (Ia) and trinexapac-ethyl.

In a further embodiment of the present invention, there is provided a composition, mixture or combination comprising a compound of Formula (Ia) and trinexapac-ethyl, which is useful to regulate plant growth and/or reduce lodging of plants. Optionally, the composition may further comprise one or more agriculturally acceptable formulation adjuvants or carriers.

In one embodiment, Formula (Ia) and trinexapac-ethyl are present in a synergistically effective amount, such that the combined effect of the active ingredients is greater than the sum of each when applied individually. A synergistic effect may be calculated using the Colby formula, as is known in the art.

In one embodiment, the weight ratio of Formula (Ia) to trinexapac-ethyl is from 1:10 to 10:1. In particular, the weight ratio of Formula (Ia) to trinexapac-ethyl is from 1:1 to 1:5, from 1:1 to 1:3, from 1:1.5 to 1:3. In certain aspects of the invention, the weight ratio of Formula (Ia) to trinexapac-ethyl is 1:1.5, 1:2, 1:2.5 or 1:3.

The compound of Formula (I) according to the invention can be used as a plant growth regulator or for lodging control by itself, but is generally formulated into a composition using formulation adjuvants, such as carriers, solvents and surface-active agents (SFAs). The composition can be in the form of concentrates which are diluted prior to use, although ready-to-use compositions can also be utilised. The final dilution is usually made with water, but can be made instead of, or in addition to, water, with, for example, liquid fertilisers, other active ingredients (e.g. insecticidal, acaracidal, nematacidal or fungicidal components), micronutrients, biological organisms, oil or solvents.

The compositions generally comprise from 0.1 to 99% by weight, especially from 0.1 to 95% by weight, of a compound of Formula (I) and from 1 to 99.9% by weight of a formulation adjuvant, which preferably includes from 0 to 25% by weight of an SFA.

The compositions can be chosen from a number of formulation types, many of which are known from the Manual on Development and Use of FAO Specifications for Plant Protection Products, 5th Edition, 1999.

These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. The compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of the compound of Formula (I). Such additives include SFAs, spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

In addition, further, other biocidally-active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, insecticides, bactericides, acaricides, nematicides and/or other plant growth regulators. Pesticidal agents are referred to herein using their common name are known, for example, from "The Pesticide Manual", 15th Ed., British Crop Protection Council 2009.

In the methods for regulating the growth of plants and/or reducing lodging in a locus according to the present invention, the application is generally made by spraying the composition, typically by tractor mounted sprayer for large areas, but other methods such as dusting (for powders), drip or drench can also be used. Alternatively, the composition may be applied in furrow or directly to a seed before or at the time of planting. In the method for promoting the germination of seeds according to the present invention, the compound of Formula (I) may be incorporated as a component in a seed treatment composition.

The compound of Formula (I) or composition of the present invention may be applied to a plant, part of the plant, plant organ, plant propagation material or a surrounding area thereof.

In one embodiment, the invention relates to a method of treating a plant propagation material comprising applying to the plant propagation material a compound of Formula (I) or a composition comprising a compound of Formula (I) in an amount effective to regulate plant growth. The invention also relates to a plant propagation material treated with a compound of Formula (I) or a composition of the present invention. Preferably, the plant propagation material is a seed.

In a further aspect of the invention, there is provided a method of treating a plant propagation material comprising applying to the plant propagation material a compound of Formula (I) or a composition comprising the compound of Formula (I) in an amount effective to regulate plant growth.

In a further aspect of the invention, there is provided a plant propagation material treated with or comprising a compound of Formula (I).

Methods for applying active ingredients to plant propagation material, especially seeds, are known in the art, and include dressing, coating, pelleting and soaking application methods of the propagation material. The treatment can be applied to the seed at any time between harvest of the seed and sowing of the seed or during the sowing process. The seed may also be primed either before or after the treatment. The compound of Formula (I) may optionally be applied in combination with a controlled release coating or technology so that the compound is released over time.

The composition of the present invention may be applied pre-emergence or post-emergence. Suitably, where the composition is being used to regulate the growth of crop plants or to enhance the yield, it may be applied pre- or post-emergence, but preferably post-emergence of the crop. Where the composition is used to promote the germination of seeds, it may be applied pre-emergence.

Plants in which the composition according to the invention can be used include crops such as cereals (for example wheat, barley, rye, oats); beet (for example sugar beet or fodder beet); fruits (for example pomes, stone fruits or soft fruits, such as apples, pears, plums, peaches, almonds, cherries, strawberries, raspberries or blackberries); leguminous plants (for example beans, lentils, peas or soybeans); oil plants (for example rape, mustard, poppy, olives, sunflowers, coconut, castor oil plants, cocoa beans or groundnuts); cucumber plants (for example marrows, cucumbers or melons); fibre plants (for example cotton, flax, hemp or jute); citrus fruit (for example oranges, lemons, grapefruit or mandarins); vegetables (for example spinach, lettuce, asparagus, cabbages, carrots, onions, tomatoes, potatoes, cucurbits or paprika); lauraceae (for example avocados, cinnamon or camphor); maize; rice; tobacco; nuts; coffee; sugar cane; tea; vines; hops; durian; bananas; natural rubber plants; turf or ornamentals (for example flowers, shrubs, broad-leaved trees or evergreens such as conifers). This list does not represent any limitation.

In one embodiment, the plants are monocotyledonous plants, for example plants selected from the group consisting of rice, wheat, barley, rye and oats.

The invention may also be used to regulate the growth, or promote the germination of seeds of non-crop plants, for example to facilitate weed control by synchronizing germination.

Crops are to be understood as also including those crops which have been modified by conventional methods of breeding or by genetic engineering. For example, the invention may be used in conjunction with crops that have been rendered tolerant to herbicides or classes of herbicides (e.g. ALS-, GS-, EPSPS-, PPO-, ACCase- and HPPD-inhibitors). An example of a crop that has been rendered tolerant to imidazolinones, e.g., imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. Methods of rendering crop plants tolerant to HPPD-inhibitors are known; for example the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria*, *Chenchrus*, *Lolium*, *Festuca*, *Setaria*, *Eleusine*, *Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaff® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g., improved storage stability, higher nutritional value and improved flavour).

EXAMPLES

Example 1: Plant Growth Regulation Trial in Rice, India

Field trials were setup during the hot season in Annanagar and Kumbakonam in India. Local rice (*Oryza sativa* L.) varieties ADT45 was mechanically transplanted at four plants per hill with a plant spacing of 16 cm and a row spacing of 30 cm. All trials were performed in good level of water management. Fertilizer application, and weed, insect and disease control were carried out in accordance with the best local practice across the trial area. Commercial treated seeds were used (with no neonicotinoid compounds present).

The trial design was a randomized bloc design, with a plot size of 40 $m^2$ (12 rows, each 4 m wide and 10 m long); each trial had four replicates. Treatments were applied at the panicle initiation growth stage (BBCH 30) as shown in the table below.

Overall trial quality was very high: there was no insect damage and no disease pressure or weeds; the plots were very homogenous. Heat stress level was low to medium with 5-10% empty spikelets in the untreated control.

TABLE 1

| | Treatment | Rate (g ai/ha) | Lodging (%) |
|---|---|---|---|
| 1 | Untreated check | n/a | 70.0 |
| 2 | Formula (Ia) | 10 g ai/ha | 29.0 |
| 3 | Formula (Ia) + MODDUS | 10 + 30 g ai/ha | 2.5 |
| 4 | Formula (Ia) | 20 g ai/ha | 56.0 |
| 5 | Formula (Ia) + MODDUS | 20 + 30 g ai/ha | 1.25 |

TABLE 1-continued

| Treatment | Rate (g ai/ha) | Lodging (%) |
|---|---|---|
| 6 | MODDUS | 30 g ai/ha | 3.0 |

MODDUS ® contains trinexapac-ethyl

The results show that the compound of Formula (Ia) significantly reduces lodging compared to the untreated control.

Additionally the results show that the mixture of Formula (Ia) with MODDUS® at rates of 20 g ai/ha and 30 g ai/ha respectively (treatment 5) gave the best results, with only 1.25% lodging; a reduction of heat stress symptoms was also observed from this treatment.

It was noted that treatment 6, MODDUS® solo, reduced lodging and plant height as expected, but no reduction of heat stress symptoms was observed.

The invention claimed is:

1. A composition, comprising: a compound of Formula (Ia)

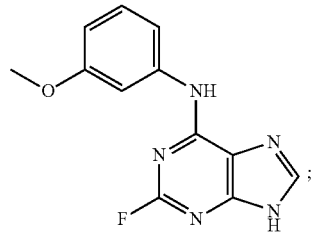

(Ia)

and trinexapac-ethyl;
wherein the compound of Formula (Ia) and trinexapac-ethyl are present in a weight ratio providing synergistic reduced lodging of plants and wherein the weight ratio of Formula (Ia) to trinexapac-ethyl is from 1:10 to 10:1.

2. The composition according to claim 1 further comprising an agriculturally acceptable formulation adjuvant.

3. The composition according to claim 1, wherein the weight ratio of Formula (Ia) to trinexapac-ethyl is from 1:1 to 1:5.

4. A method for reducing lodging of plants, comprising applying to the plants, plant part, plant propagation material or plant growing locus during the reproductive growth stage of the crop plants, a composition according to claim 1.

5. The composition according to claim 1, wherein the only agrochemical active ingredients are the compound of Formula (Ia) and trinexapac-ethyl.

6. The composition according to claim 5, wherein the weight ratio of Formula (Ia) to trinexapac-ethyl is from 1:1.5 to 1:3.

7. A composition, comprising: a compound of Formula (Ia)

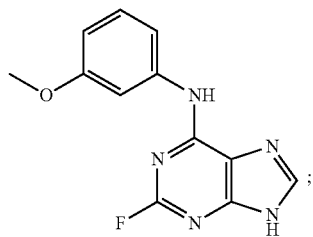

(Ia)

and trinexapac-ethyl;
wherein the weight ratio of Formula (Ia) to trinexapac-ethyl is from 1:1.5 to 1:3.

8. The composition according to claim 7, wherein the only agrochemical active ingredients are the compound of Formula (Ia) and trinexapac-ethyl.

* * * * *